United States Patent [19]

Sabahi

[11] Patent Number: 5,683,618
[45] Date of Patent: *Nov. 4, 1997

[54] REFRIGERATION COMPOSITIONS IN WHICH THE LUBRICANT COMPRISES AT LEAST ONE ESTER, KETOESTER, OR ESTER-NITRILE OIL

[75] Inventor: Mahmood Sabahi, Baton Rouge, La.

[73] Assignee: Albemarle Corporation, Richmond, Va.

[*] Notice: The term of this patent shall not extend beyond the expiration date of Pat. No. 5,399,279.

[21] Appl. No.: 593,153

[22] Filed: Feb. 1, 1996

Related U.S. Application Data

[63] Continuation-in-part of Ser. No. 268,064, Jun. 28, 1994, abandoned, which is a continuation of Ser. No. 974,628, Sep. 21, 1992, abandoned, which is a continuation-in-part of Ser. No. 812,398, Dec. 23, 1991, abandoned.

[51] Int. Cl.$^6$ .......................... C09K 5/04; C10M 105/20; C10M 105/36; C10M 105/56
[52] U.S. Cl. ...................... 252/68; 252/167; 508/447; 508/465; 508/496
[58] Field of Search .................... 252/68, 67; 508/447, 508/465, 496

[56] References Cited

U.S. PATENT DOCUMENTS

| | | | |
|---|---|---|---|
| 2,396,626 | 3/1946 | Wiest et al. | 260/464 |
| 5,021,179 | 6/1991 | Zehler et al. | 252/68 |
| 5,145,594 | 9/1992 | Anton et al. | 252/68 |
| 5,300,245 | 4/1994 | Sawada et al. | 252/68 |
| 5,399,279 | 3/1995 | Sabahi et al. | 252/67 |
| 5,538,661 | 7/1996 | Dawson et al. | 252/68 |

FOREIGN PATENT DOCUMENTS 2-38578  8/1990  Japan.

*Primary Examiner*—Christine Skane
*Attorney, Agent, or Firm*—Philip M. Pippenger

[57] ABSTRACT

Lubricants having a viscosity suitable for a refrigeration lubricant as well as good miscibility with common refrigerants (including R-134a) comprise at least one oil corresponding to the formula $Z-C(E)(E')_p-Q_s$ in which Z is alkyl, cycloalkyl, or $-(CTT'-CT''G)_w-CTT'-CHT''G$; Q is $-(CTT'-CT''G)_t-CTT'-CHT''G$; T, T', and T'' are independently selected from hydrogen G', and organic groups containing up to 20 carbons; E, E', G, and G' are independently selected from $-COOR$, $-C(O)R'$, and $-CN$ electron withdrawing groups wherein R and R' represent hydrocarbyls containing 1–30 carbons, with the proviso that at least about 50% of the electron withdrawing groups are $-COOR$; p is zero or one; s is respectively two or one; and each of t and w represents zero or a positive integer.

18 Claims, No Drawings

REFRIGERATION COMPOSITIONS IN WHICH THE LUBRICANT COMPRISES AT LEAST ONE ESTER, KETOESTER, OR ESTER-NITRILE OIL

CROSS-REFERENCE TO RELATED APPLICATIONS

This application is a continuation-in-part of application Ser. No. 08/268,064, filed Jun. 28, 1994, now abandoned, which in turn is a continuation of Ser. No. 07/947,628, filed Sep. 21, 1992, now abandoned, which in turn is a continuation-in-part of Ser. No. 07/812,398, filed Dec. 23, 1991, now abandoned.

FIELD OF INVENTION

The invention relates to refrigeration compositions and more particularly to such compositions containing novel lubricants.

BACKGROUND

Many natural and synthetic materials are known to be useful as lubricants, their utility in particular applications depending on factors such as their stability and viscosity under the conditions of use, their pour points, and their compatibility with any materials with which they will be used.

In refrigeration applications (e.g., home-use or industrial-use refrigerators, freezers, or air conditioners for buildings, automobiles, airplanes, and other vehicles), the need to replace chlorofluorocarbon refrigerants with a refrigerant having lesser ozone-depleting potential has made it important to find lubricants which would be suitable for use with 1,1,1,2-tetrafluoroethane (R-134a), a refrigerant that has been reported to have an ozone depletion potential of zero. Mineral oils, usually the refrigeration lubricants of choice in the past, cannot be utilized in this application because of incompatibility with R-134a.

As shown, e.g., in Jolley, "New and Unique Lubricants for Use in Compressors Utilizing R- 134a Refrigerant," pp. 145-152 (a paper presented at the ASHRE/Refrigeration/-Compressor Engineering Conference at Purdue, July 1990), U.S. Pat. No. 4,944,890 (Deeb et al.), and Japanese Kokai Hei 2(1990)-173195 (Akime et al.), oils of various types, including polyalkylene glycols, esters, amides, fluorinated hydrocarbons, and ether-nitriles, have been found to have sufficient compatibility with R-134a to justify further investigation. However, there is still a need for lubricants to be used in this application, as well as in other lubricant applications.

The Michael reaction is a known process wherein a Michael acceptor (such as an $\alpha,\beta$-ethylenically-unsaturated aldehyde, ester, nitrile, ketone, sulfone, or sulfoxide) is reacted with a Michael donor (such as a dialkyl malonate) to elongate a carbon chain. U.S. Pat. No. 2,396,626 (Wiest et al.) teaches that products useful as plasticizers or solvents can be obtained by reacting two molecules of acrylonitrile, an alkyl acrylate, or an acrylamide with a molecule of a donor, such as an ester, amide, or nitrile of malonic acid, phenylacetic acid, cyanoacetic acid, or acetoacetic acid. However, as indicated in Skarzewski, "The Michael Reaction of Methanetricarboxylic Esters. A Simple Method for Two-Carbon Chain Elongation," *Synthesis*, December 1990, pp. 1125-1127, it has usually been considered undesirable to add a donor molecule to more than one acceptor molecule in such a reaction.

SUMMARY OF INVENTION

The invention resides in compositions comprising one part by weight of a refrigerant and, as a refrigeration lubricant, 0.001–1 part by weight of at least one oil corresponding to the formula $Z-C(E)(E')_p-Q_s$ in which Z is alkyl, cycloalkyl, or $-(CT'T'-CT''G)_w-CT'T'-CHT''G$; Q is $-(CT'T'-CT''G)_t-CT'T'-CHT''G$; T, T', and T" are independently selected from hydrogen, G', and organic groups containing up to 20 carbons; E, E', G, and G' are independently selected from $-COOR$, $-C(O)R'$, and $-CN$ electron withdrawing groups wherein R and R' represent hydrocarbyls containing 1–30 carbons, with the proviso that at least about 50% of the electron withdrawing groups are $-COOR$; p is zero or one; s is respectively two or one; and each of t and w represents zero or a positive integer.

DETAILED DESCRIPTION

Although the lubricants utilizable in the compositions of the invention include all of the $Z-C(E)(E')_p-Q_s$ oils defined above, those which are most suitable for use in any specific compositions vary with the particular refrigerant employed and with the conditions to which the refrigeration composition will be exposed. However, the particularly preferred lubricants are usually selected from:

(A) $Z-C(E)(E')_p-Q_s$ mixtures in which p and s are one; Z is $-(CT'T'-CT''G)_w-CT'T'-CHT''G$; and the sum of t and w in the molecules is 0–30, preferably an average of 1–10, and (B) $Z-C(E)(E')_p-Q$ mixtures in which s is two; Z is $-(CT'T'-CT''G)_w-CT'T'-CHT''G$; and the sum of t and w in the molecules is 0–30, preferably 1–10.

The refrigerants with which the novel lubricants are employed may be one or more of a wide variety of such materials, e.g., ammonia; alcohols such as methanol and ethanol; glycols such as ethylene and propylene glycols; and hydrocarbons such as methane, ethane, propane (R-290), butane, ethylene, and propylene. However, they are more commonly halocarbons and/or halohydrocarbons such as chlorotrifluoromethane, dichlorodifluoromethane, dichlorofluoromethane, chlorodifluoromethane (R-22), 1,2,2-trifluoro-1,1,2-trichloroethane, 1,1-dichloro-2,2,2-trifluoroethane (R-123), 1,1-dichloro-1-fluoroethane, 1-chloro-2,2,2-trifluoroethane, 1-chloro- 1,2,2,2-tetrafluoroethane (R-124), 1-chloro- 1,1,2,2-tetrafluoroethane, dichloromethane, difluoromethane (R-32), 1,1,2,2,2-pentafluoroethane (R-125), 1,1,2,2-tetrafluoroethane (R-134), 1,1,1,2-tetrafluoroethane (R-134a), 1,1,1-trifluoroethane (R-143a), and 1,1-difluoroethane (R-152a). The preferred refrigerants, of course, are the fluorohydrocarbons—especially R-134a—and fluorohydrocarbon mixtures.

Among the refrigerant blends with which the lubricants can be advantageously used are the binary mixtures of R-32 with R-125, R-152a, or R-134a; R-125/R-143a, R-290/R-134a, and R-22/R-152a binary blends; and ternary blends such as R-22/R-290/R-125, R-22/R-152a/R-124, R-32/R-125/R-134a, and R-125/R-143a/R-134a.

In choosing a lubricant for use with any of these refrigerants, it is important to select one which is completely miscible with the refrigerant throughout the temperature range to which the refrigeration composition is to be exposed and which has a viscosity such as to permit its functioning as a lubricant over that entire temperature range. The optimum lubricant to be used in any instance can be determined by routine experimentation, aided by observation of the following general principles:

(1) Miscibility with refrigerants is enhanced by the presence of short side chains in the oil molecules.
(2) A low viscosity is most suitable for a lubricant to be used at relatively low temperatures, while lubricants intended for use at relatively high temperatures should have higher viscosities.
(3) Viscosity is increased by the presence of long side chains in the molecules as well as by having a larger number of side chains therein; and variations in viscosity may thus be achieved by varying the number of long-chain groups in the oils, increasing or decreasing their molecular weights, and/or widening or narrowing their molecular weight distributions.
(4) The viscosities most suitable for lubricants to be used in refrigeration compositions that are to be exposed to the temperature conditions generally found in refrigeration equipment (i.e., temperatures in the range of about −40° C. to 70° C. or sometimes even higher temperatures) are apt to be 1–600, preferably 5–300, and most preferably 10–200 $mm^2.s^{-1}$ at 40° C.; and it is frequently also desirable for the lubricant to have a viscosity index $\geq 100$.

The lubricants of the invention have a structure such as to make it most convenient to prepare them via a Michael-type reaction, preferably such a reaction which permits the incorporation of 1–30 molecules of Michael acceptor per molecule of Michael donor.

When produced directly by a Michael reaction, the lubricants are prepared by reacting one or more Michael donors with one or more Michael acceptors to form a Z—C(E)(E')$_p$—Q$_s$ product which is an oil. However, it is frequently preferred to prepare the lubricants by conducting such a Michael reaction to form a first Z—C(E)(E')$_p$—Q$_s$ product (often not an oil) which is then subjected to one or more additional reactions, such as transesterification, alkylation, cyanation, hydrolysis, or esterification, to convert it to a Z—C(E)(E')$_p$—Q$_s$ product that has functional groups different from the electron withdrawing groups in the intermediate product and is an oil.

Michael donors and acceptors which can be used in the reaction are compounds which have one or more electron withdrawing groups attached to an organic group which is hydrocarbyl or at least predominantly hydrocarbyl in nature, i.e., (1) contains only carbon and hydrogen or (2) contains carbon, hydrogen, and one or more other atoms but contains so few of the other atoms that the predominantly hydrocarbyl nature of the group is preserved.

When a predominantly hydrocarbyl R or R' group (or any other predominantly hydrocarbyl group mentioned hereinafter) contains atoms other than carbon and hydrogen, these other atoms may be part of a chain or ring as hetero atoms, such as oxygen, sulfur, or phosphorus atoms; or they may be present in substituent groups, such as alkoxy, halo, or cyano groups. However, to preserve the predominantly hydrocarbyl nature of the group, the number of hetero atoms or non-hydrocarbyl substituents therein should not exceed 0.3 per carbon and is preferably not more than 0.1 per carbon. These predominantly hydrocarbyl groups can be regarded as being virtually the same as the alkyl, cycloalkyl, aralkyl, and alkenyl groups to which they most closely correspond, so terms such as alkyl, cycloalkyl, aralkyl, and alkenyl, as used hereinafter, should be understood as including the predominantly hydrocarbyl groups as well as the hydrocarbyl groups normally denoted by those terms (except, of course, when the terms are qualified in such a way as to make it clear that they could not refer to the predominantly hydrocarbyl groups—as when the groups contain too few carbons to permit the inclusion of any hetero atoms while fulfilling the requirement of containing $\leq 0.3$ such atoms per carbon.)

In each of the reactants employed to prepare the products of the invention, the electron withdrawing groups are selected from —COOR, —C(O)R', and —CN groups in which R and R' represent hydrocarbyl groups of up to 30, preferably 1–20, and more preferably 1–10 carbons. The electron withdrawing groups may be the same or different, whether they are present in the same reactant or in different reactants.

Michael donors which can be used in the reaction are compounds corresponding to the formula Z'—CH(E)(E") wherein Z' is hydrogen or an alkyl or cycloalkyl group of up to 10 carbons, E is a —COOR, —C(O)R', or —CN electron withdrawing group, and E" is hydrogen or a —COOR, —C(O)R', or —CN electron withdrawing group—R and R' in these formulas usually representing alkyl or cycloalkyl groups of up to 30, preferably up to 20, and more preferably up to 10 carbons, most preferably methyl or ethyl. When a single Michael donor is employed in the reaction, each E in the Z—C(E)(E')$_p$—Q$_s$ product is the same, as is each E' in that product. However, when a mixture of two or more donors is used, different molecules of the product will contain different E and/or E' groups when the donors contain different E and/or E" groups.

Exemplary of utilizable donors are (1) the methyl, ethyl, propyl, isopropyl, butyl, isobutyl, t-butyl, pentyl, hexyl, chlorohexyl, heptyl, octyl, decyl, bromodecyl, ethoxyoctyl, cyclopropyl, cyclopentyl, cyclohexyl, and cyclooctyl esters of alkanoic and substituted alkanoic acids such as acetic, cyanoacetic, propionic, and butyric acids, (2) the corresponding diesters of 1,1 -dicarboxyalkanes and other dicarboxyalkanes (e.g., succinic, glutaric, and higher acids of the oxalic acid series) in which the alkane moiety is a divalent hydrocarbylene radical derived from an alkane such as methane, ethane, propane, isopropane, butane, isobutane, t-butane, pentane, hexane, heptane, octane, propoxypentane, butoxypentane, nonane, decane, or ethoxyoctane; (3) the corresponding diesters of 1,1-dicarboxy-1-cycloalkylmethanes in which the cycloalkyl substituent is cyclopropyl, cyclopentyl, cyclohexyl, or cyclooctyl; (4) the corresponding dicyano- and diacyl-substituted alkanes and cycloalkylmethanes in which the acyl groups are acetyl, propionyl, butyryl, or isobutyryl; and (5) the corresponding cyano- or acyl-substituted alkanoic and cycloalkylethanoic acid esters. Because of their permitting rapid reaction and leading to the formation of products which can be easily converted to oils, the most preferred Michael donors are the dimethyl and diethyl malonates; the methyl and ethyl cyanoacetates, acetoacetates; propionylacetates; malononitrile; acetonitrile; and dipropionylmethane.

Michael acceptors which may be reacted with these donors are CTT'=CT"G compounds in which T, T', and T" are independently selected from hydrogen, G', and organic groups (usually hydrocarbyl or predominantly hydrocarbyl groups, such as alkyl, alkoxyalkyl, alkylthioalkyl, cycloalkyl, dialkylaminocycloalkyl, aryl, haloaryl, alkoxyaryl, aralkyl, and alkaryl groups) of up to 20 carbons, preferably 1–10 carbons, with the proviso that at least one of T, T', and T" must be hydrogen; and G and G' are electron withdrawing groups selected from the —COOR, —C(O)R', and —CN groups described above.

Examples of utilizable acceptors are (1) the methyl, ethyl, propyl, isopropyl, butyl, isobutyl, t-butyl, pentyl, hexyl, chlorohexyl, heptyl, octyl, decyl, bromodecyl, ethoxyoctyl, dodecyl, cyanododecyl, tetradecyl, hexadecyl, octadecyl, eicosyl, cyclopropyl, cyclopentyl, cyclohexyl, and cyclooctylesters of acrylic, methacrylic, ethacrylic, crotonic, and cinnamic acids, (2) the corresponding esters of 1-carboxy-1-cyanoethylene and the corresponding diesters of 1,1-dicarboxy-2-cyanoethylene and 1,1-dicarboxyethylene, and (3) nitriles such as acrylonitrile, methacrylonitrile, ethacrylonitrile, dicyanoethylene, and tricyanoethylene, as well as the corresponding compounds in which the α- or β-carbon bears an organic substituent such as a propyl, isopropyl, butyl, isobutyl, t-butyl, pentyl, hexyl, chlorohexyl, heptyl, octyl, ethylthiohexyl, decyl, bromodecyl, cyanodecyl, ethoxyoctyl, cyclopropyl, cyclopentyl, cyclohexyl, cyclooctyl, N,N-dimethylaminocyclohexyl, methylphenyl, bromophenyl, ethoxyphenyl, or benzyl group, etc.

Of these compounds, the Michael acceptors which are apt to be most preferred are (A) those in which T, T', and T" are hydrogen and G is a —COOR, —C(O)R', or —CN group wherein R and R' are methyl or ethyl and (B) the corresponding compounds in which one or two of the hydrogens represented by T, T', and T" is replaced with a G' electron withdrawing group which may be the same as G or a different group selected from —CN, —COOR, and —C(O)R'. The especially preferred Michael acceptors are the methyl and ethyl acrylates, acrylonitrile, dicyanoethylene, and tricyanoethylene.

When a single Michael acceptor is employed in the reaction, each T, T', T", and G in the product is the same as each other T, T', T", and G. However, when a mixture of two or more acceptors is used and the different acceptors have different T, T', T", G, and/or G' groups in their molecules, those differences will be reflected in the product. For example, when methyl acrylate and methyl methacrylate are simultaneously or consecutively reacted with a Michael donor, each T and T' in the product molecules will represent hydrogen and each G will represent a —COOCH$_3$ group; but some of the T" groups will represent hydrogen, while the others will be methyl groups. Similarly, when methyl acrylate and acrylonitrile are simultaneously or consecutively reacted with a donor, each T, T', and T" in the product molecules will represent hydrogen; but some of the G groups will be —COOCH$_3$ while others will be —CN.

The reaction between the Michael donor and Michael acceptor may sometimes be conducted by a process such as that of Wiest et al., the teachings of which are incorporated herein by reference. However, it is generally preferred to react the donor and acceptor in the presence of a basic compound and a phase transfer catalyst at a suitable temperature, usually a temperature of about 0°–150° C., preferably about 20°–80° C., and most preferably about 40°–60° C.

The basic compound, which serves to initiate the reaction, is preferably an alkali or alkaline earth metal hydroxide, alkoxide, amide, or carbonate, more preferably a sodium or potassium hydroxide, alkoxide, amide, or carbonate, and most preferably potassium carbonate. However, any other suitable base may be employed, and it is sometimes desirable to utilize a weaker base, such as an alkali or alkaline earth metal bicarbonate (especially potassium bicarbonate) to minimize polymerization of the Michael acceptor. Although the base may be used in any amount sufficient to initiate the reaction, its concentration is usually about 1–50%, preferably 3–30%, and most preferably 5–10%, based on the weight of the Michael donor.

The phase transfer catalyst employed in the process may be any such catalyst having sufficient catalytic activity to permit the addition of the desired number of Michael acceptor molecules to the Michael donor at a desired rate. Such catalysts include common phase transfer catalysts such as aluminum oxide, potassium fluoride, and mixtures thereof. However, the preferred catalysts are ordinarily alkylammonium salts such as tetraalkylammonium chlorides, bromides, fluorides, iodides, sulfates, hydrogen sulfates, carbonates, and phosphates in which the alkyl groups contain 1–20 carbons—salts which are frequently used as phase transfer catalysts. The phase transfer catalyst is used in a catalytic amount, typically an amount such as to provide about 0.1–1 tool of catalyst per tool of Michael donor.

Although this Michael reaction is usually conducted in the absence of a solvent, it may sometimes be desirable to increase the efficiency of the phase transfer reaction by utilizing a solvent. The solvent, when used, should be a non-nucleophilic substance, e.g., a hydrocarbon, which will maintain the reactants in solution during the reaction but permit easy separation of the products from the reaction mixture. Such solvents include, e.g., toluene, xylene, other alkylbenzenes, hexane, and other saturated hydrocarbons.

The reaction is effected by combining the reactants, initiator, and catalyst, optionally in the presence of a solvent, and maintaining contact between the reactants at the selected reaction temperature until the desired degree of reaction has been effected. It is sometimes preferred to make the Michael acceptor the last of the ingredients to be charged to the reaction vessel in order to achieve better control of the reaction temperature and hence improved direction of the reaction to the formation of a desired product.

In the Michael reaction, the type of product formed is determined largely by the acceptor/donor ratio in the reaction mixture—higher ratios leading to the formation of products containing more acceptor moieties per molecule and thus having higher molecular weights and higher viscosities. Since the reaction normally leads to the formation of a mixture of products containing different numbers of acceptor moieties per molecule, it permits the production of some molecules containing more acceptor moieties than the number that would theoretically be provided by the amount of acceptor employed in the reaction mixture. However, it is necessary for the reaction mixture to contain at least the stoichiometric requirement of the acceptor, and preferably a stoichiometric excess, in order for the product to contain a substantial mount of a desired product molecule. Thus, e.g., when a product containing three acceptor moieties is desired, the reaction mixture should contain at least the stoichiometrically required three mols of acceptor/mol of donor and preferably contains >3 mols of acceptor/tool of donor; and, when a product containing eight acceptor moieties is desired, it is important for the reaction mixture to contain at least eight mols of acceptor/mol of donor.

Since the oils having optimum viscosities are usually those in which the molecules contain 1–30 acceptor moieties/donor moiety, it is generally preferred for the acceptor/donor mol ratio in the reaction mixture to be about 1–35/1, more preferably about 1–10/1.

Different Michael reactions which can be used to form products containing more acceptor moieties than the number of active hydrogens in the donors are illustrated in the following equations:

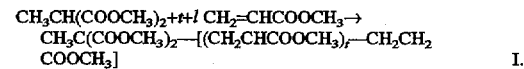

I.

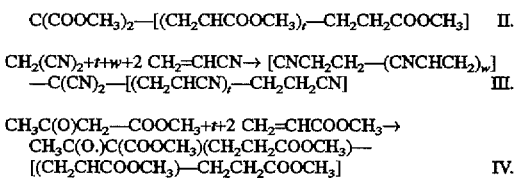

$$C(COOCH_3)_2\text{—}[(CH_2CHCOOCH_3)_t\text{—}CH_2CH_2COOCH_3] \quad \text{II.}$$

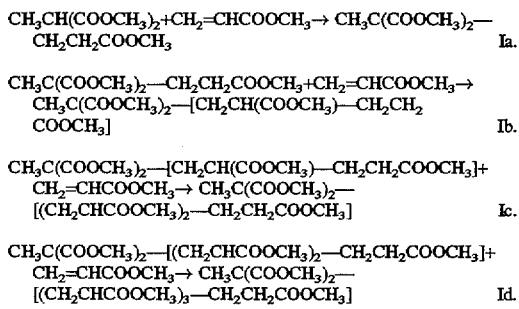

$$CH_2(CN)_2 + t + w + 2\ CH_2\text{=}CHCN \rightarrow [CNCH_2CH_2\text{—}(CNCHCH_2)_w]$$
$$\text{—}C(CN)_2\text{—}[(CH_2CHCN)_t\text{—}CH_2CH_2CN] \quad \text{III.}$$

$$CH_3C(O)CH_2\text{—}COOCH_3 + t + 2\ CH_2\text{=}CHCOOCH_3 \rightarrow$$
$$CH_3C(O.)C(COOCH_3)(CH_2CH_2COOCH_3)\text{—}$$
$$[(CH_2CHCOOCH_3)_t\text{—}CH_2CH_2COOCH_3] \quad \text{IV.}$$

These reactions are able to proceed until the desired number of acceptor moieties have been combined with the donor, even when the donor contains only one active hydrogen, because the hydrogen donated to an acceptor moiety when the donor is deprotonated becomes an active hydrogen in the acceptor moiety and can be donated to a second moiety where it becomes a donatable hydrogen again. Thus, a reaction such as that summarized in Equation I above would proceed as follows:

$$CH_3CH(COOCH_3)_2 + CH_2\text{=}CHCOOCH_3 \rightarrow CH_3C(COOCH_3)_2\text{—}CH_2CH_2COOCH_3 \quad \text{Ia.}$$

$$CH_3C(COOCH_3)_2\text{—}CH_2CH_2COOCH_3 + CH_2\text{=}CHCOOCH_3 \rightarrow$$
$$CH_3C(COOCH_3)_2\text{—}[CH_2CH(COOCH_3)\text{—}CH_2CH_2COOCH_3] \quad \text{Ib.}$$

$$CH_3C(COOCH_3)_2\text{—}[CH_2CH(COOCH_3)\text{—}CH_2CH_2COOCH_3] +$$
$$CH_2\text{=}CHCOOCH_3 \rightarrow CH_3C(COOCH_3)_2\text{—}$$
$$[(CH_2CHCOOCH_3)_2\text{—}CH_2CH_2COOCH_3] \quad \text{Ic.}$$

$$CH_3C(COOCH_3)_2\text{—}[(CH_2CHCOOCH_3)_2\text{—}CH_2CH_2COOCH_3] +$$
$$CH_2\text{=}CHCOOCH_3 \rightarrow CH_3C(COOCH_3)_2\text{—}$$
$$[(CH_2CHCOOCH_3)_3\text{—}CH_2CH_2COOCH_3] \quad \text{Id.}$$

and continue in the presence of a sufficient amount of acceptor.

As indicated by Equations II and III above, the incorporation of several acceptor moieties into the product molecules is facilitated by utilizing the more reactive $CH_2(E)$ (E") donors, especially when a $CH_2$=CHG acceptor is employed; and the incorporation of multiple acceptor moieties is also aided by the use of (1) reactants containing the stronger electron withdrawing groups, (2) the higher reaction temperatures, (3) the stronger catalysts, and/or (4) the larger amounts of catalyst. Variations in product structure and properties can be achieved by using mixtures of donor compounds and/or mixtures of acceptor compounds in the reaction.

The products of the Michael reaction may be liquids or solids, depending on the particular reactants and reactant ratios used; and, as already indicated, they are typically mixtures of compounds containing different numbers of acceptor moieties per molecule. If desired, the individual compounds of the mixture or groups of those compounds (e.g., the relatively low and relatively high molecular weight fractions) may be separated from one another prior to being used in their end application or prior to being subjected to additional reactions preparatory to such use. However, such separations are frequently unnecessary and, in fact, sometimes undesirable. Having a product characterized by a wide molecular weight distribution can be an advantage in providing a balance of properties, as is the case with oils which are to be used in refrigeration compositions wherein some relatively high molecular weight portion is desired to give a required viscosity, but some relatively low molecular weight portion is desired to impart compatibility with the refrigerant with which the oil is to be used.

Achieving either a better balance of properties or properties which differ in some other respect from those of the Michael reaction product can also be accomplished by subjecting the product mixture or one or more of the components thereof to one or more of the reactions known to be capable of converting functional groups (i.e., E, E', G, and/or G' groups) in the compounds to different groups. Such reactions, such as the conversion of lower ester groups to higher ester groups, or the conversion of nitriles to esters and/or amides, can be conducted by conventional techniques, such as those indexed and outlined in Harrison and Harrison, *Compendium of Organic Synthetic Methods*, Wiley-Interscience (New York), 1971, the teachings of which are incorporated herein by reference.

In addition to having the aforementioned advantage, the post-treatment of the Michael reaction product to prepare a different compound or product mixture of the invention has the benefit of facilitating the preparation of products which it would be at least more difficult to prepare directly by the Michael reaction. For example, it can be beneficial to use a post-Michael reaction conversion of the functional groups when the desired end product is to contain functional groups which, if present in the Michael reactants, would make the Michael reaction relatively slow. Thus, it is apt to be preferred, for example, to react dimethyl malonate with methyl acrylate to provide a first product (which is a solid rather than an oil) and then transesterify that product with hexanol to provide an oily second product in which the functional groups are hexyl ester groups than to prepare an oily Michael reaction product from the slower-reacting dimethyl or dihexyl malonate and hexyl acrylate.

Particularly preferred lubricants of the invention are ester oils (including ketoester and ester-nitrile oils) in which at least about 50% (preferably at least about 75%) of the functional groups are ester groups, as well as the oils in which all of the functional groups are ester groups prepared by (1) reacting a Z'—CH(E)(COOR) donor in which Z' is most preferably hydrogen (e.g., dimethyl malonate, methyl acetoacetate, or methyl cyanoacetate) with a CTT'=CT"COOR acceptor (e.g., methyl acrylate) to form a Z—C(E)(COOR)—(CTT'—CT"COOR)$_w$—CTT'—CHT"COOR product composed primarily of molecules wherein Z is most preferably —(CTT'—CT"COOR)$_t$—CTT'—CHT"COOR, at least some of the R's (which may be the same or different) are lower alkyls of 1–8 carbons, each of t and w is zero or a positive integer, and the sum of t and w is 0–28 and (2) when desired (especially when all of the R's are methyl) tramesterifying the resultant intermediate product by reacting it with one or more alcohols containing more carbons per molecule than the lower alkyl groups of the intermediate. An especially preferred embodiment of the invention resides in the use of such ester oils which are prepared so as to have at least three acceptor molecules in at least about 25%, more preferably at least about 40% of the molecules obtained by the Michael reaction.

In the preparation of these preferred oils, the intermediate product may be recovered from its synthesis reaction mixture and, if desired, may also be fractionated into separate components before being subjected to transesterification. However, it is frequently preferable to transesterify the intermediate without first separating it from its synthesis reaction mixture.

Regardless of whether the transesterification is conducted on a recovered or unrecovered intermediate, it is accomplished by contacting the intermediate with one or more alcohols containing more carbons per molecule than the alkyl groups to be replaced and maintaining contact between the reactants at a suitable temperature until the desired transesterification has been effected. Alcohols most apt to be desirable for use in the reaction are substituted and unsubstituted alkanols, cycloalkanols, and aralkanols containing up to about 30 carbons (e.g., ethanol, chloroethanol, propanol, butanol, hexanol, bromohexanol, heptanol, octanol, decanol, fluorodecanol, dodecanol, hexadecanol, octadecanol, eicosanol, tetracosanol, triacontanol, cyclohexanol, cyclooctanol, benzyl alcohol, p-methylbenzyl alcohol, phenethyl alcohol, phenylpropanol, phenylpentanol, and phenethylbenzyl alcohol), as well as the aliphatic, cycloaliphatic, and araliphatic alcohols containing up to 30 carbons and also containing hetero atoms, such as oxygen, phosphorus, or sulfur (e.g., ethylthioethanol, ethoxyethanol, and the like).

The amount of alcohol employed in the transesterification reaction varies with the degree of transesterification desired, the quantity generally being the stoichiometric amount or an amount slightly in excess of the stoichiometric requirement. For example, when the intermediate contains an average of four ester groups per molecule, and it is wished to replace substantially all of those ester groups with the alcohol or alcohols used in the transesterification reaction, the amount of alcohol added to the intermediate should be at least four mols/mol of intermediate. Only about half as much alcohol would be added, on the other hand, when the objective is to replace approximately half of the ester groups of the intermediate.

Use of a transesterification reaction after completion of the Michael reaction permits a wide variety of products to be prepared from any particular product of the Michael reaction—final products having only the short ester chains which favor solubility in a refrigerant such as R-134a, final products having only the longer ester chains which increase viscosity, and final products having a controlled mix of short and longer ester chains to provide desired intermediate degrees of solubility and viscosity.

The transesterification is suitably conducted at an elevated temperature which provides for reflux and removal of a lower alcohol by-product from the reaction mixture without permitting undue loss of the higher alcohol reactant(s) from the reaction vessel, e.g, a temperature of about 50°–180° C. Although the reaction does not require catalysis, it is accelerated by the use of a base, which may be the base already present when the Michael reaction product is transesterified without first being recovered from its synthesis reaction mixture. It is sometimes desirable to add a catalytic amount of a base to accelerate the reaction, especially when the Michael product has been recovered before being subjected to transesterification. However, when such an addition is made, the amount of catalyst added is preferably kept low enough to prevent interference with the reaction or with subsequent separation of the products from the reaction mixture. Such an amount is typically about 0.05–1.0 g/kg of the Michael reaction product to be transesterified.

In another embodiment of the invention, desirable ester products can be obtained by subjecting a Michael reaction product containing nitrite groups to simultaneous hydrolysis and esterification with one or more alcohols containing 1–30, preferably 1–20, and more preferably 1–10 carbons in order to convert some or all of the nitrile groups to ester groups. The Michael reaction product treated in this manner may be a product already containing some ester groups (such as a product obtained by reacting methyl cyanoacetate with methyl acrylate or acrylonitrile or by reacting malononitrile with methyl acrylate) or a non-ester product, such as that obtained by reacting malononitrile with acrylonitrile. When this technique is employed in the preparation of the lubricants, the hydrolysis and esterification may be conducted by conventional techniques—the reactant proportions being selected as in the transesterification reaction described above to convert all or only some of the nitrile groups to ester groups.

The products resulting from the Michael reaction or from conversion of the Michael reaction products to derivatives are typically washed with water to remove any unreacted materials and catalyst prior to being used in their intended application; and, if desired, they may then be further purified by subjecting them to fractional distillation.

Refrigeration compositions of the invention typically comprise 0.001–1, preferably 0.1–1 part of the novel lubricant per part by weight of the refrigerant, and, if desired, they may also contain additives of the type conventionally used in refrigeration lubricants. In addition to epoxy and other dehydrating agents sometimes employed to prevent corrosion of refrigeration equipment by any water in the refrigeration compositions, such additives include, e.g., oxidation resistance and thermal stability improvers, corrosion inhibitors, metal deactivators, lubricity additives, viscosity index improvers, pour and/or floc point depressants, detergents, dispersants, antifoaming agents, anti-wear agents, and extreme pressure resistance additives, such as those exemplified in U.S. Pat. No. 5,021,179 (Zehler et al.), the teachings of which are incorporated herein by reference. As in Zehler et al., these additives, when employed, are generally utilized in small amounts totaling not more than 8%, preferably not more than 5%, of the weight of the lubricant formulation.

The refrigeration compositions are generally formed prior to use. However, when desired, they may also be formed in situ during operation of the refrigeration equipment. Thus, the refrigerant and the lubricant may be charged to the refrigeration equipment separately, either simultaneously or consecutively in either order, instead of being preblended.

Although the invention is advantageous in its provision of refrigeration compositions containing other refrigerants, its greatest value is in its ability to provide refrigeration compositions containing lubricants which are suitable for use with refrigerants and refrigerant mixtures that are environmentally superior to the chlorofluorocarbon reffigerants most commonly used in refrigeration applications—especially fluorohydrocarbons such as R-134a. The lubricants of the invention include many which have sufficient miscibility with R-134a to be utilizable therewith. However, the lubricants which are apt to be preferred in this regard are the ROOC—$CH_2CH_2$—(ROOC—$CHCH_2$)$_w$—C(COOR)$_2$—($CH_2CHCOOR$)$_t$—$CH_2CH_2COOR$ oily mixtures in which the R's represent one or more alkyl groups of 1–10 carbons and the sum of t and w in the molecules is an average of 0–10. Of these preferred lubricants, those which are most preferred are usually the mixtures in which all of the R groups are isopropyl or in which at least 10% of the R groups are $C_1$–$C_4$ alkyl groups and at least 50% of the R groups are alkyl groups of 4–10 carbons.

The use of these preferred lubricants in refrigeration compositions containing R-134a or other fluorohydrocarbon lubricant has the unexpected advantage of permitting the compositions additionally to contain known ester oils which otherwise could not be satisfactorily employed in such compositions because of lacking sufficient miscibility with fluorohydrocarbons. Such known ester oils include, e.g., alkyl alkanoates, alkyl diesters of aliphatic and aromatic dicarboxylic acids, and higher fatty acid esters of neopolyols. When it is wished to utilize any of these known ester oils in a fluorohydrocarbon-containing refrigeration composition, the known ester oil is employed together with a fluorohydrocarbon-miscibility-improving amount of a preferred ester lubricant of the present invention—normally an amount such as to provide a novel ester lubricant/known ester oil weight ratio of at least about 0.05/1, preferably at least 0.1/1, more preferably 0.5–5.0/1, and most preferably 1–5/1.

The following examples are given to illustrate the invention and are not intended as a limitation thereof.

EXAMPLE 1

Charge a suitable reaction vessel with 792 g (6 mols) of dimethyl malonate, 52.8 g (0.4 mol) of potassium carbonate, 12 g (0.035 mol) of tetrabutylammonium hydrogen sulfate, and 1290 g (15 mols) of methyl acrylate. After stirring the reaction mixture at room temperature for about 18 hours, slowly heat it to about 50° C. to effect a rapid rise of the temperature of the reaction mixture to reflux. Maintain the reaction mixture at reflux for about 15 minutes and then cool to room temperature over a period of about 1 hour. A heavy solid mass forms in the bottom of the reaction vessel during cooling. Dilute this mass with methylene chloride, wash with five 1.5-L portions of water, and subject the product to gas chromatographic (GC) analysis. The analysis shows the product to consist, in area percentages, of 4.3% trimethyl ester of 1,1,3-propanetricarboxylic acid, 70% tetramethyl ester of 1,3,3,5-pentanetetracarboxylic acid, 18% pentamethyl ester of 1,3,3,5,7-heptanepentacarboxylic acid, and 7.7% polyesters, i.e., products having more than five ester groups per molecule. Isolate the triester and tetraester components by fractional distillation under reduced pressure.

EXAMPLE 2

Conduct two additional Michael reactions between dimethyl malonate and methyl acrylate using tetrabutylammonium hydrogen sulfate as the phase transfer catalyst as in Example 1 but employing sodium methoxide as the base, 80° C. as the reaction temperature, and methyl acrylate/ dimethyl malonate mol ratios of 8/1 (reaction mixture 2-A) and 10/1 (reaction mixture 2-B) respectively. Monitor the reactions by GC and discontinue them when the following analyses are obtained:

| Reaction Mixture | Analysis |
|---|---|
| 2-A | 32% tetramethyl ester of 1,3,3,5-pentanetetracarboxylic acid, 24% pentamethyl ester of 1,3,3,5,7-heptanepentacarboxylic acid, 11% hexamethyl ester of 1,3,5,5,7,9-nonanehexacarboxylic acid, 8% heptamethyl ester of 1,3,5,5,7,9,11-undecaneheptacarboxylic acid, 2% octamethyl ester of 1,3,5,7,7,9,11,13-tridecaneoctacarboxylic acid, and smaller amounts of higher esters |
| 2-B | 20% tetramethyl ester, 22% pentamethyl ester, 19% hexamethyl ester, 14% heptamethyl ester, 9% octamethyl ester, and smaller amounts of higher esters |

Then work up the product mixtures by diluting them with solvent, washing to neutrality with water, and removing solvent, water, and lower boiling products by distillation to form viscous oils which, in each case, are completely miscible with R-134a over a temperature range of −40° C. to 70° C.

EXAMPLE 3

Charge a suitable reaction vessel with 660 g (5 mols) of dimethyl malonate, 35 g (0.25 mol) of potassium carbonate, and 1.75 g (0.005 mol) of tetrabutylammonium hydrogen sulfate. Heat the stirred mixture to 120° C., and add 2048 g (16 mols) of n-butyl acrylate over a period of six hours while monitoring the reaction by GC, which shows the dibutyl dimethyl ester of 1,3,3,5-pentanetetracarboxylic acid to be the major product at the end of this period. Then heat the reaction mixture at 150° C. for three hours to form a product mixture containing the tributyl dimethyl ester of 1,3,3,5,7-heptanepentacarboxylic acid. Cool the resulting reaction mixture to room temperature, add water and toluene, wash repeatedly with water until neutral, remove the water and toluene by azeotropic distillation, and then remove light products at 180°–185° C. and 0.1–0.15 mmHg to provide a heavy oil having a viscosity of 96 $mm^2.s^{-1}$ at 40 ° C., a viscosity of 11.6 $mm^2.s^{-1}$ at 100° C., a viscosity index of 109, and excellent miscibility with R-134a over a temperature range of −60° C. to 80° C.

EXAMPLE 4

Using a dimethyl malonate/methyl acrylate Michael reaction and workup procedure similar to that of the preceding examples, prepare a 20.8 g sample of a mixture of 66% tetramethyl ester of 1,3,3,5-pentanetetracarboxylic acid, 26% pentamethyl ester of 1,3,3,5,7-heptanepentacarboxylic acid, and 6% hexamethyl and heptamethyl esters. Treat the mixture with 0.1 mol of butanol and 0.1 mol of hexanol at 120° C. in the presence of a catalytic amount of 10% sodium methoxide, remove the volatiles by distillation, and work up to provide an oil which has a viscosity of 159 $mm^2.s^{-1}$ at 40° C., a viscosity of 14.6 $mm^2.s^{-1}$ at 100° C., a viscosity index of 88, and total miscibility with R-134a.

EXAMPLE 5

Using a Michael reaction and workup procedure similar to that of the preceding examples except for replacing the dimethyl malonate with methyl acetoacetate, prepare a mixture composed predominantly of the trimethyl ester of 3-acetyl-1,3,5-pentanetricarboxylic acid and tetramethyl ester of 3-acetyl-1,3,5,7-heptanetetracarboxylic acid. Then treat that product with an equimolar mixture of butanol and hexanol as in Example 4 to replace about 85% of the methyl groups with butyl and hexyl groups and provide a keto ester oil which is miscible with R-134a.

EXAMPLE 6

Using a Michael reaction and workup procedure similar to that of the preceding examples except for replacing the dimethyl malonate with methyl cyanoacetate, prepare a mixture composed predominantly of the trimethyl ester of 3-cyano-1,3,5-pentanetricarboxylic acid and tetramethyl ester of 3-cyano-1,3,5,7-heptanetetracarboxylic acid. Then treat that product with an equimolar mixture of butanol and hexanol as in Example 4 to replace about 80% of the methyl groups with butyl and hexyl groups and provide an esternitrile oil which is miscible with R-134a.

EXAMPLE 7

Charge a suitable reaction vessel with 660 g (2.2 mols) of the tetramethyl ester of Example 1, 406 g (4.4 mols) of n-butanol, 560 g (4.4 mols) of n-hexanol, and 5 mL of 5% sodium methoxide. Stir the reaction mixture magnetically and heat to about 110 ° C. to result in the slow distillation of methanol. After removing a stoichiometric amount of methanol, cool the reaction mixture to room temperature and dilute with toluene. After washing with water, remove the solvent and distill the crude oil under reduced pressure. The fraction collected at 195°–220° C. and 0.11–0.14 mm Hg is a water-white oil containing the tetraester product. This oil is miscible with R-134a refrigerant over a temperature range of −40° C. to 70° C. and has a viscosity of 20–30 $mm^2.s^{-1}$ at 40° C., a viscosity index of 100, and a total acid number (TAN) of <0.05 mg KOH/gram.

EXAMPLE 8

Transesterify a crude reaction mixture of 85% 1,5-dibutyl-3,3-dimethyl ester of 1,3,3,5-pentanetetracarboxylic acid with 21 g (0.16 mol) of 2-ethyl-1-hexanol at 150°–200° C. under nitrogen. After removing the stoichiometric amount of methanol, cool the reaction mixture, dilute with toluene, wash to neutrality with water, and remove the water and toluene by azeotropic distillation. The resultant oil has a viscosity of 62.9 $mm^2.s^{-1}$ at 40° C., a viscosity of 7.9 $mm^2.s^{-1}$ at 100° C., a viscosity index of 88, and total miscibility with R-134a.

EXAMPLE 9

Transesterify a 3,3-diethyl-1,5-dimethyl ester of 1,3,3,5-pentanetetracarboxylic acid with n-butanol in the presence of a catalytic amount of sodium methoxide by the general procedure of Example 5. The resulting product is totally miscible with R-134a refrigerant, has a viscosity of 19.2 $mm^2.s^{-1}$ at 40° C., a viscosity of 3.6 $mm^2.s^{-1}$ at 100° C., and a viscosity index of 40.

EXAMPLE 10

Repeat Example 9 except for replacing the butanol with a 1/1/1 mixture of n-hexanol, n-heptanol, and n-octanol. The resulting product is totally miscible with R-134a refrigerant at temperatures of 0°–70° C., has a viscosity of 22.3 $mm^2.s^{-1}$ at 40° C., a viscosity of 4.4 $mm^2.s^{-1}$ at 100° C., and a viscosity index of 107.

EXAMPLE 11

Charge a reaction vessel with 15.8 Kg (120 mols) of dimethyl malonate, 158 g (1.2 mols) of potassium carbonate, and 37 g (0.1 mol) of tetrabutylammonium hydrogen sulfate under nitrogen. Heat the reactor to about 70° C., add 25.8 Kg (300 mols) of methyl acrylate over six hours, and then heat the reaction mixture at 70°–80° C. for at least 10 hours to form a product mixture containing a major amount of tetramethyl ester of 1,3,3,5-pentanetetracarboxylic acid, smaller amounts of pentamethyl and higher esters, and a minor amount of trimethyl ester of 1,1,3-propanetricarboxylic acid.

Charge 22 Kg (296 mols) of n-butanol and 30.3 Kg (296 mols) of n-hexanol to the reactor and heat at 110°–120° C. while collecting the volatiles overhead. After removing the stoichiometric amount of methanol, cool the reaction mixture to room temperature, dilute with toluene, wash to neutrality with water, dry by the azeotropic removal of water, and heat treat the crude under reduced pressure.

Distillation under reduced pressure (1 mmHg) and 200°–250° C. provides an oil which has a viscosity of 17 $mm^2.s^{-1}$ at 40° C., a viscosity of 3.6 $mm^2.s^{-1}$ at 100° C., a total acid number (TAN) of 0.025 mg KOH/g, a water content of 64 ppm, and total miscibility with R-134a over a temperature range of −60° C. to 80° C. The bottoms product is an oil having a viscosity of 24.8 $mm^2.s^{-1}$ at 40° C., a viscosity of 4.7 $mm^2.s^{-1}$ at 100° C., a total acid number of 0.034 mgKOH/g, a water content of 73 ppm, and total miscibility with R-134a over a temperature range of −60° C. to 80° C.

EXAMPLE 12

Charge a reaction vessel with 3.3 g (0.05 mol) of malononitrile, 0.7 g (0.005 mol) of potassium carbonate, and 0.17 g (0.5 mmol) of tetrabutylammonium hydrogen sulfate under nitrogen. Slowly add 11.2 g (0.2 mol) of acrylonitrile at 50° C. with stirring and maintain the temperature at 50°–70° C. for 3 hours. Then cool the reaction mixture to room temperature, dissolve in ethyl acetate, wash with water until neutral, dry over magnesium sulfate, filter, and concentrate to provide a solid mass which spectroscopic analysis indicates to contain more than two acrylonitrile moieties per molecule. Heat this product at 110°–120° C. in the presence of 5.4 g (0.3 mol) of water, 3.2 g (0.1 mol) of methanol, 7.4 g (0.1 mol) of n-butanol, 10.2 g (0.1 mol) of n-hexanol, and 18 g (0.5 mol) of HCl gas to convert the nitrile groups to ester groups and form an oil which is miscible with R-134a.

EXAMPLE 13

Charge a reaction vessel with 3.3 g (0.05 mol) of malononitrile, 0.7 g (0.005 mol) of potassium carbonate, and 0.17 g (0.5 mmol) of tetrabutylammonium hydrogen sulfate. Heat the mixture to 50° C. under nitrogen and slowly add 21.6 g (0.25 mol) of methyl acrylate at a rate such as to maintain the temperature under 80° C. Keep the reaction mixture at 70°–80 ° C. for two hours, cool to room temperature, dilute with dichloromethane, wash with water until neutral, dry over magnesium sulfate, filter, and concentrate to provide a solid mass which spectroscopic analysis shows to contain dimethyl ester of 3,3-dicyano-1,5-pentanedicarboxylic acid, trimethyl ester of 5,5-dicyano-1,3,7-heptanetricarboxylic acid, and smaller amounts of higher molecular weight components. Heat this product at 110°–120° C. in the presence of 14.8 g (0.2 mol) of n-butanol, 20.4 g (0.2 mol) of n-hexanol, 0.9 g (0.05 mol) of water, and 5.5 g (0.15 mol) of HCl gas to replace about 80% of the methyl groups with butyl and hexyl groups and form an ester-nitrile oil which is miscible with R-134a.

What is claimed is:

1. A refrigeration composition comprising one pan by weight of a refrigerant and, as a refrigeration lubricant, 0.001–1 part by weight of at least one oil corresponding to the formula Z—C(E)(E')$_p$—Q$_s$ in which Z is alkyl, cycloalkyl, or —(CTT'—CT"G)$_w$—CTT'—CHT"G; Q is —(CTT'—CT"G)$_t$—CTT'—CHT"G; T, T', and T" are independently selected from the group consisting of hydrogen and G'; E, E', G, and G' are independently selected from the group consisting of —COOR, —C(O)R', and —CN electron withdrawing groups wherein R and R' represent hydrocarbyls containing 1–30 carbons, with the proviso that at least about 50% of the electron withdrawing groups are —COOR; p is zero or one; s is respectively two or one; and each of t and w represents zero or a positive integer.

2. The composition of claim 1 wherein the lubricant is a Z—C(E)(E')$_p$—Q$_s$ mixture in which s is two, Z is —(CTT'—CT"G)$_w$—CTT'—CHT"G, and the sum of t and w in the molecules is 0–30.

3. The composition of claim 2 wherein the sum of t and w in the molecules is an average of 1–10.

4. The composition of claim 1 wherein the lubricant is a Z—C(E)(E')$_p$—Q$_s$ mixture in which p and s are one, Z is —(CTT'—CT"G)$_w$—CTT'—CHT"G, and the sum of t and w in the molecules is 0–30.

5. The composition of claim 4 wherein the sum of t and w in the molecules is an average of 1–10.

6. The composition of claim 4 wherein the lubricant is an ROOC—CH$_2$CH$_2$—(ROOC—CHCH$_2$)$_w$—C(E)(COOR)—(CH$_2$CHCOOR)$_t$—CH$_2$CH$_2$COOR oily mixture in which the R's represent one or more alkyl groups of 1–10 carbons and the sum of t and w in the molecules is an average of 0–10.

7. The composition of claim 6 wherein E is —CN.

8. The composition of claim 6 wherein E is —C(O)R' in which R' represents an alkyl group of 1–10 carbons.

9. The composition of claim 6 wherein E is —COOR.

10. The composition of claim 9 wherein the lubricant is an oily mixture prepared by (1) reacting one molar proportion of dimethyl malonate with about 1–10 molar proportions of methyl acrylate in the presence of a nucleophilic compound and a phase transfer catalyst to form a Michael reaction product having at least three methyl acrylate moieties in at least 25% of the molecules and (2) reacting the Michael reaction product with at least one alkanol containing 4–10 carbons to replace at least 50% of the methyl groups in that product with alkyl groups containing 4–10 carbons.

11. The composition of claim 1 wherein the refrigerant comprises a halocarbon and/or a halohydrocarbon.

12. The composition of claim 11 wherein the refrigerant comprises at least one fluorohydrocarbon.

13. The composition of claim 12 wherein the refrigerant is 1,1,1,2-tetrafluoroethane.

14. The composition of claim 13 which is a miscible mixture of 1,1,1,2-tetrafluoroethane and an ROOC—$CH_2CH_2$—$(ROOC$—$CHCH_2)_w$—$C(E)(COOR)$—$(CH_2CHCOOR)_t$—$CH_2CH_2COOR$ lubricant mixture in which the R's represent one or more alkyl groups of 1–10 carbons and the sum of t and w in the molecules is an average of 0–10.

15. The composition of claim 14 wherein E is —CN.

16. The composition of claim 14 wherein E is —C(O)R' in which R' represents an alkyl group of 1–10 carbons.

17. The composition of claim 14 wherein E is —COOR.

18. The composition of claim 17 wherein the lubricant is an oily mixture prepared by (1) reacting one molar proportion of dimethyl malonate with about 1–10 molar proportions of methyl acrylate in the presence of a nucleophilic compound and a phase transfer catalyst to form a Michael reaction product having at least three methyl acrylate moieties in at least 25% of the molecules and (2) reacting the Michael reaction product with at least one alkanol containing 4–10 carbons to replace at least 50% of the methyl groups in that product with alkyl groups containing 4–10 carbons.

* * * * *